(12) United States Patent
Smith

(10) Patent No.: US 12,343,313 B2
(45) Date of Patent: Jul. 1, 2025

(54) PACIFIER FABRICATION METHOD

(71) Applicant: Jessica Smith, Wichita, KS (US)

(72) Inventor: Jessica Smith, Wichita, KS (US)

( * ) Notice: Subject to any disclaimer, the term of this patent is extended or adjusted under 35 U.S.C. 154(b) by 318 days.

(21) Appl. No.: 18/135,512

(22) Filed: Apr. 17, 2023

(65) Prior Publication Data

US 2023/0248616 A1    Aug. 10, 2023

(51) Int. Cl.
| | | |
|---|---|---|
| *A61F 2/52* | (2006.01) | |
| *A61J 17/00* | (2006.01) | |
| *B29C 33/38* | (2006.01) | |
| *B29L 31/00* | (2006.01) | |
| *A41C 3/04* | (2006.01) | |
| *A41D 1/215* | (2018.01) | |
| *A61F 2/50* | (2006.01) | |

(52) U.S. Cl.
CPC ............ *A61J 17/001* (2015.05); *A61F 2/52* (2013.01); *A61J 17/105* (2020.05); *B29C 33/3878* (2013.01); *A41C 3/04* (2013.01); *A41D 1/215* (2018.01); *A61F 2002/5053* (2013.01); *A61F 2002/526* (2013.01); *B29C 2033/3871* (2013.01); *B29L 2031/7412* (2013.01); *B29L 2031/7532* (2013.01)

(58) Field of Classification Search
CPC ......... B29C 33/3878; B29C 2033/3871; B29L 2031/7412; A61F 2/52; A61F 2002/526; A61F 2002/5053
See application file for complete search history.

(56) References Cited

U.S. PATENT DOCUMENTS

| | | | |
|---|---|---|---|
| 4,199,825 A | * | 4/1980 | Knoche ............ A61F 2/52 |
| | | | 450/55 |
| 4,335,067 A | | 6/1982 | Castanis et al. |
| 5,108,686 A | | 4/1992 | Griffin |
| 5,653,732 A | | 8/1997 | Sheehy |

(Continued)

FOREIGN PATENT DOCUMENTS

| | | | | |
|---|---|---|---|---|
| CA | 2773304 A1 | * | 10/2013 | ............ A61F 2/12 |
| DE | 102012108216 A1 | * | 3/2014 | ........... A61F 2/5046 |

(Continued)

OTHER PUBLICATIONS

"Custom-Made Baby Bottle Nipples", mamilo.co. https://www.mamilo.co/.

(Continued)

*Primary Examiner* — Benjamin A Schiffman
(74) *Attorney, Agent, or Firm* — Kenneth H. Jack; Davis & Jack, LLC

(57) ABSTRACT

A method for fabricating a pacifier having surface features replicating those of a nursing mother's nipple, wherein the nipple has a length, the method including steps of utilizing the nursing mother's nipple as a positive mold to cast a first negative mold; utilizing the first negative mold to cast a replica of the nursing mother's nipple; modifying the replica of the nursing mother's nipple so that said replica has a length greater than that of the nursing mother's nipple; utilizing the modified replica of the nursing mother's nipple as a second positive mold to cast a second negative mold; and utilizing the second negative mold to cast an extended length replica of the nursing mother's nipple.

12 Claims, 9 Drawing Sheets

(56) References Cited

U.S. PATENT DOCUMENTS

| | | | |
|---|---|---|---|
| 5,700,288 A * | 12/1997 | Eaton | A41C 3/148 |
| | | | 450/55 |
| 5,824,075 A | 10/1998 | Thielbar | |
| 6,136,027 A * | 10/2000 | Jackson | A61F 2/5046 |
| | | | 623/7 |
| 6,207,874 B1 * | 3/2001 | Felton | B44C 1/105 |
| | | | 602/42 |
| 6,253,935 B1 | 7/2001 | Fletcher | |
| 6,660,204 B1 * | 12/2003 | Clover, Jr. | A61F 2/52 |
| | | | 264/222 |
| 6,669,064 B2 | 12/2003 | Perricone | |
| 6,736,830 B2 | 5/2004 | Roust | |
| RE40,487 E | 9/2008 | Eaton | |
| 7,566,344 B2 * | 7/2009 | Hansen | A61F 2/52 |
| | | | 623/7 |
| 8,961,562 B2 | 2/2015 | Randolph et al. | |
| 9,044,380 B2 | 6/2015 | Sabree et al. | |
| 10,016,342 B2 | 7/2018 | Kempker et al. | |
| 10,449,121 B2 | 10/2019 | Bolten | |
| 10,780,024 B2 | 9/2020 | Lofaro et al. | |
| 10,932,993 B2 | 3/2021 | Gledhill | |
| 11,076,969 B2 * | 8/2021 | Meikle | A61B 5/165 |
| 11,305,463 B2 | 4/2022 | Wright | |
| 11,357,707 B2 | 6/2022 | Zeev | |
| 11,413,134 B1 * | 8/2022 | Catalano | A61F 2/12 |
| 2004/0010311 A1 * | 1/2004 | Reynolds | A61F 2/52 |
| | | | 623/7 |
| 2004/0143325 A1 * | 7/2004 | Holmes | A61F 2/52 |
| | | | 623/7 |
| 2004/0143326 A1 * | 7/2004 | Holmes | A61F 2/52 |
| | | | 623/7 |
| 2004/0156934 A1 * | 8/2004 | Francalacci Franca | |
| | | | B29C 33/40 |
| | | | 623/7 |
| 2008/0071370 A1 * | 3/2008 | Vinas | A61F 2/52 |
| | | | 623/7 |
| 2008/0314776 A1 | 12/2008 | Cooke | |
| 2018/0104156 A1 * | 4/2018 | Mobbs | B29C 64/393 |
| 2019/0053918 A1 * | 2/2019 | Weir | A61F 2/52 |
| 2019/0104967 A1 | 4/2019 | Dretzka-Kaye et al. | |
| 2020/0060940 A1 | 2/2020 | Conneely et al. | |
| 2024/0238104 A1 * | 7/2024 | Van Beek | B29C 64/188 |

FOREIGN PATENT DOCUMENTS

| | | | | |
|---|---|---|---|---|
| WO | WO2009-130454 | | 10/2009 | |
| WO | WO-2009130454 A1 * | 10/2009 | | A61F 2/5046 |
| WO | WO-2022187907 A1 * | 9/2022 | | |

OTHER PUBLICATIONS

"Impression Kit", pink-perfect.com. https://www.pink-perfect.com/product/impression-kit/.

"Replacement Nipple", mimijumi.com. https://www.mimijumi.com/products/replacement-nipple.

* cited by examiner

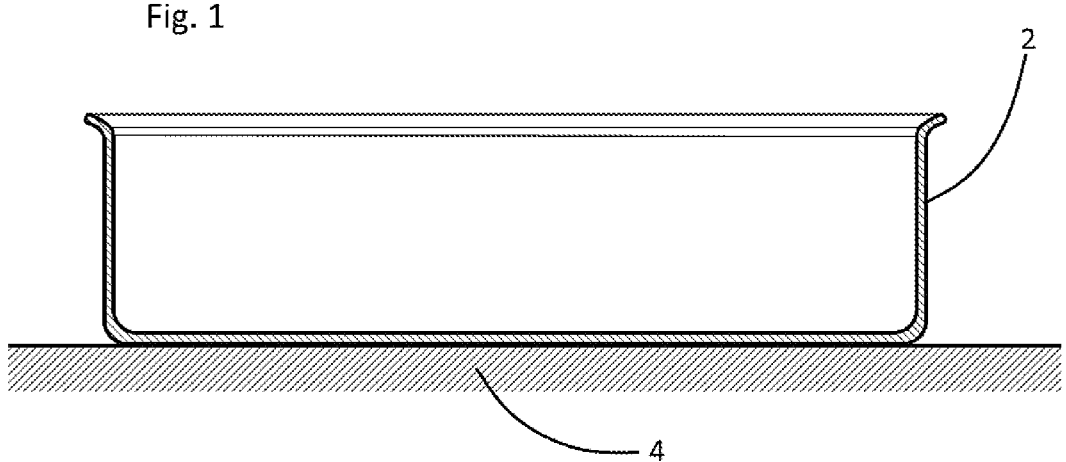
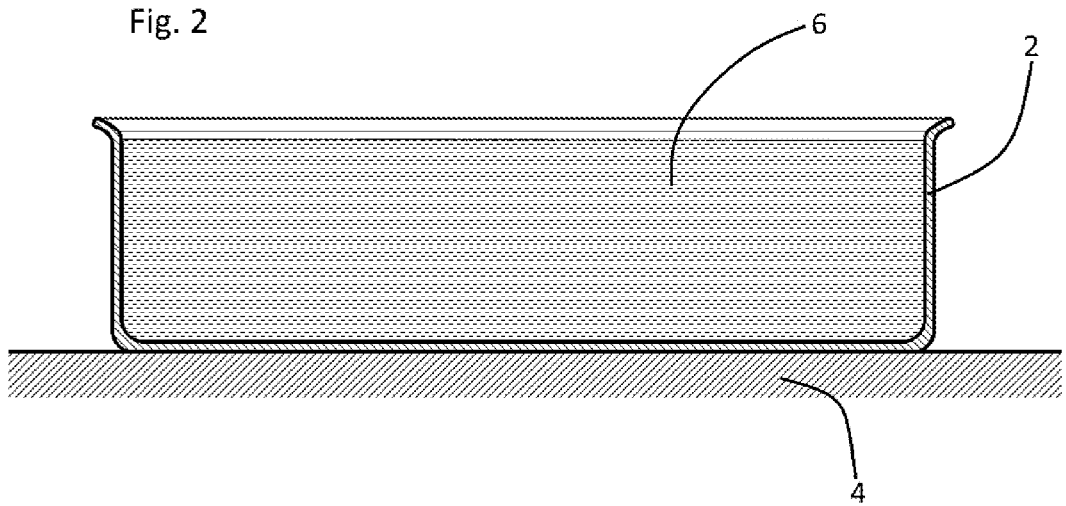

PACIFIER FABRICATION METHOD

FIELD OF THE INVENTION

This invention relates to methods for casting and molding pacifiers for use by infants. More particularly, the instant invention relates to such methods which are adapted to incorporate within surfaces of the pacifier, replications of the surface textures, protrusions, and indentations that are present upon the surface of the nipple of the infant's mother.

BACKGROUND OF THE INVENTION

At a commencement of nursing or suckling, a breast fed infant commonly orally latches onto her mother's breast, bringing the mother's nipple and the areola into contact with the infant's lips and tongue. Orally induced negative pressure imposed upon the breast during suckling tends to elastically lengthen the nipple, and tends to deform or deflect the areola ventrally or in the direction of the nipple. Such suckling induced deformations tend to cause the effective length of the nipple during suckling to be greater than the nipple's resting dorsal to ventral dimension.

For purposes of enhancing an infant's tactile familiarity with a pacifier, which increases the infant's acceptance of the pacifier, pacifiers are known to include specially molded replications of the surface texture of the mother's nipple. In such specially molded infant pacifiers, the surface variations present upon the pacifier's nipple portion mimic the texture of the mother's nipple. A problem associated with such pacifier fabrication technique and method arises or is recognized when the infant actively applies negative suckling pressure to such pacifier. The suckling pressure induced extensions of the effective length of the mother's natural nipple and areola often are not reproduced during suckling upon a nipple texture replicating pacifier. Such nipple texture replicating pacifiers typically do not significantly elastically extend in the ventral direction in response to the infant's oral suckling action. As a result of such difference or deficit, the infant's oral tactile perception of the nipple texture replicating pacifier differs from the infant's tactile perception of her mother's natural nipple. Due to such tacitly perceived differences, commonly known nipple texture replicating pacifiers are often rejected by the infant.

The instant inventive pacifier fabrication method solves or ameliorates problems and challenges described above by incorporating and utilizing specialized fabrication steps which replicate in a pacifier both the effective dorsal to ventral length of the mother's nipple and texture of the mother's nipple.

BRIEF SUMMARY OF THE INVENTION

The instant invention comprises a method for fabricating an infant pacifier of the type which incorporates surface textures matching those of the nipple and/or areola surfaces of the infant's nursing mother. In a first step of the instant inventive method, the nursing mother's nipple is utilized as or in the manner of a positive mold to form or cast a first negative mold. Thereafter, such first negative mold is used to form or cast a substantially exact replica of the nursing mother's nipple. In such nipple replica, surface textures, protrusions, and indentations of the mother's natural nipple are advantageously accurately reproduced.

In a subsequent step of the instant inventive method, the cast replica of the nursing mother's nipple is modified so that it has a dorsal to ventral length dimension that is greater than that of the dorsal to ventral length of the nursing mother's natural nipple. In a preferred mode of performance of the method, such length modification ventrally extends the nipple replica between ¼ and ¾ inches.

In a further fabrication step of the instant inventive method, the length modified replica of the nursing mother's nipple is utilized as a second positive mold to form or cast a second negative mold which, similarly with the function of the first negative mold, is capable of accurately replicating surface texture of the mother's nipple. According to the instant inventive method, such second negative mold is further capable of replicating a dorsal to ventral nipple length extension similar to that imposed by the infant upon the natural nipple during suckling. In a further step of the instant inventive method the second negative mold is utilized to finally form such extended length replica of the nursing mother's nipple.

The instant method's steps of utilizing the nursing mother's nipple as a first positive mold to form a first negative mold suitably entail a prevision of a shallow upwardly opening vessel which contains a volume of semi-liquid molding material. Alginate, semi-liquid silicone, polyurethane resin, semi-liquid latex, urethane resin, semi-liquid plaster, or epoxy resin are suitably used. Also in the method's preferred mode of performance, the nursing mother's nipple is initially downwardly inserted into the provided upwardly opening vessel, and into the semi-liquid molding material contained therein. Such downward motion of the breast preferably continues until both the nipple and the areola surrounding the nipple are downwardly impressed into the molding material. Such initially performed method steps advantageously allow surface textures of both the nipple and the areola to be reproduced in a finally cast extend length nipple replica which serves as an infant pacifier.

During use of an infant pacifier fabricated in accordance with the steps of the instant inventive method, the suckling induced ventral extensions of nipple and of surrounding areola into the infant's mouth are advantageously reproduced via the instant invention's step of incorporation of a nipple extension component in the nipple molding process. Such length extending molding steps advantageously mimic the natural nipple length extension which is tactilely perceived by the infant during suckling upon her mother's breast. The instant inventive method promotes infant pacifier acceptance by replicating the natural texture of her mother's nipple, and by further replicating the length of such nipple during suckling.

Accordingly objects of the instant inventions include the performance of method and process steps set forth above for the enhancement of infant pacifier acceptance.

Other and further objects, benefits, and advantages of the instant invention will become known to those skilled in the art upon review of the Detailed Description which follows, and upon review of the appended drawings.

BRIEF DESCRIPTION OF THE DRAWINGS

FIG. 1 is a sectional view of an upwardly opening vessel which may be provided and utilized in accordance with the steps of the instant inventive infant pacifier fabrication method.

FIG. 2 redepicts the structure of FIG. 1, the view of FIG. 2 additionally showing a body of semi-liquid molding material contained within the vessel.

DETAILED DESCRIPTION OF THE INVENTION

Figure 3:
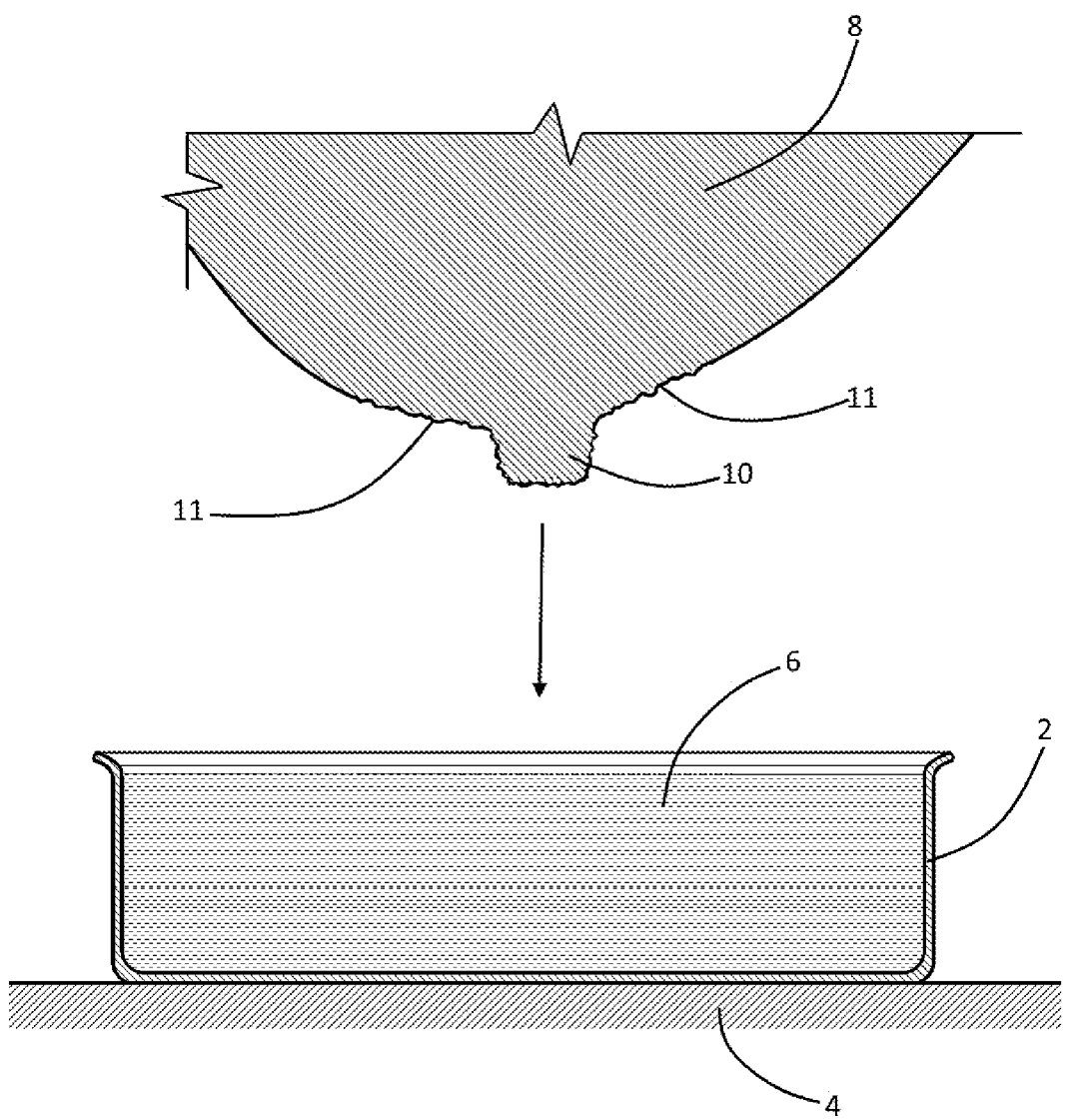
FIG. 3 redepicts the structure of FIG. 2, the view of FIG. 3 additionally showing, in sectional view, a ventral portion of a lactating mother's breast overlying said vessel.

Referring now to the drawings, and in particular drawing FIG. 1, an upwardly opening vessel 2 is preferably provided, such vessel being placed upon a flat work surface such as a counter or table top 4. Referring further to FIG. 2 such vessel 2 may be filled with a semi-liquid molding material such as water saturated alginate. Other suitably used semi-liquid molding materials include silicone, polyurethane resin, latex, urethane resin, plasters, and epoxy resin.

Figure 4:
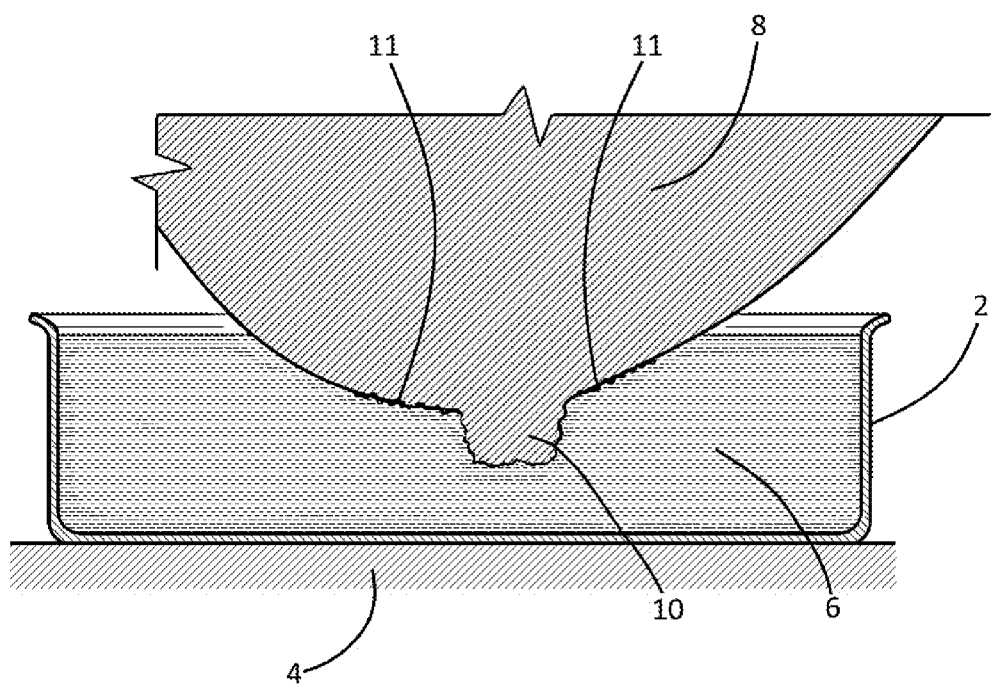
FIG. 4 redepicts the structure of FIG. 3, the view of FIG. 4 showing the nipple and areola portions of the breast of FIG. 3 downwardly inserted into the semi-liquid molding material.

Referring further to FIG. 3, a breast 8 of a nursing mother may be positioned over the upper opening of vessel 2, the breast 8 overlying the upper surface of the molding material 6. Referring further to FIG. 4, the breast 8 is then downwardly moved toward and into the molding material 6 until the nipple 10 and the areola 11 surrounding the nipple 10 extend into and impress the molding material 6. Such downward extension of the breast 8 into the molding material 6 utilizes the breast 8 as a positive mold, such positive mold being capable of forming a nipple replicating negative mold.

Figure 5:
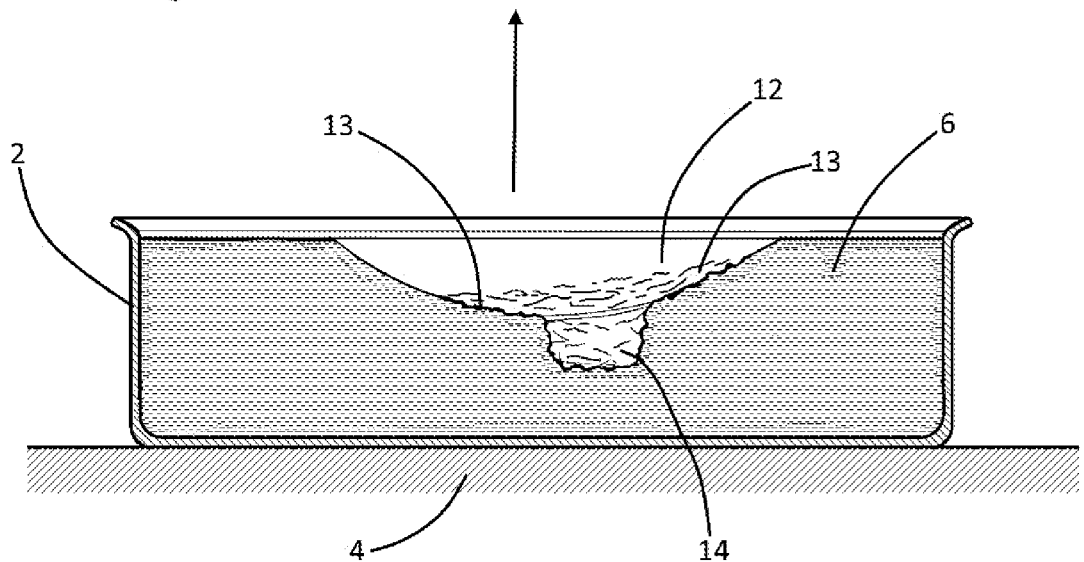
FIG. 5 redepicts the structure of FIG. 4, the view of FIG. 5 showing the breast of FIG. 4 upwardly removed.

Thereafter, referring further to FIG. 5, the breast 8 may be upwardly withdrawn from the molding material 6. Such upward withdrawal leaves an imprint or concavity 12 within the molding material 6, such concavity's surface advantageously presenting both areola texture replicating indentations and protrusions 13 and nipple texture replicating indentations and protrusions 14. Upon hardening and setting of molding material 6, such body of material constitutes a first negative mold which may be upwardly removed from the vessel 2, Referring further to FIG. 6 the concavity 12, including its texture replicating indentations and protrusions 13 and 14 advantageously constitutes and may function as a first negative mold which is capable of replicating the mother's nipple 10 and areola 11.

Figure 7:
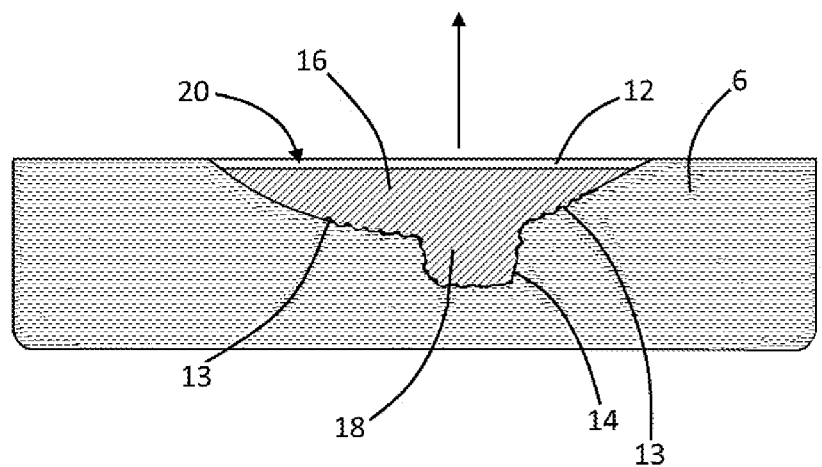
FIG. 7 redepicts the structure of FIG. 6, the view of FIG. 7 showing a thermosetting plastic material filling the concavity of the mold of FIG. 6.
Figure 8:
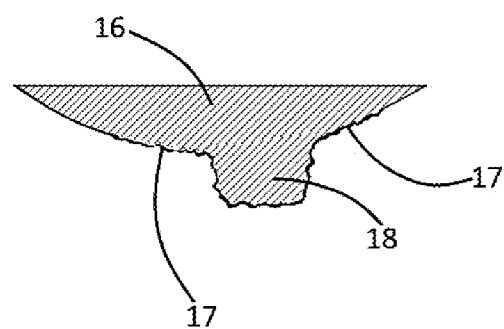
FIG. 8 redepicts the structure of FIG. 7, the view FIG. 8 showing a cast replication of the breast's nipple and areola, such replica having been upwardly removed from the mold of FIG. 7.

Referring further to FIG. 7 the first negative mold 12 may be filled with a thermosetting plastic material 16, such as silicone. Thereafter, referring further to FIG. 8, upon hardening and setting, a substantially exact silicone plastic replica of the nipple 10 and areola 11 may be upwardly withdrawn from the first negative mold or concavity 12. In such cast replica 16, the surface texture of its ventral nipple section 18 substantially matches the texture of the mother's natural nipple 10, and the texture of the areola section 17 similarly substantially exactly matches the texture of the mother's natural areola 11.

Figure 9:
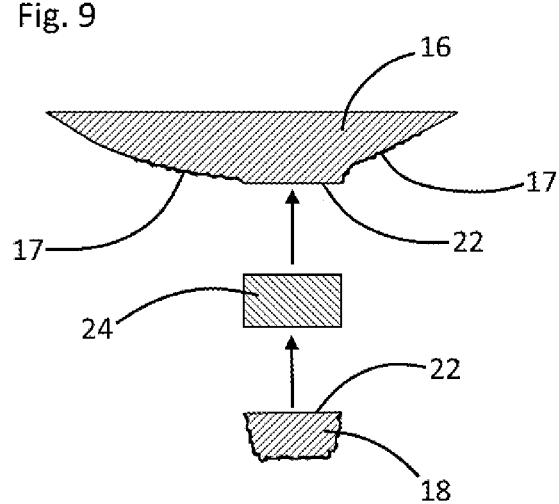
FIG. 9 redepicts the structure of FIG. 8, the view of FIG. 9 showing a sectioning or segmenting of a nipple portion and showing of an extension member or segment positioned between the cloven nipple portions.

Thereafter, referring further to FIG. 9 the nipple section 18 of the cast replica 16 may be cut at a traverse sectioning line 22, the nipple replica 16 is suitably cleaved by a knife blade to temporarily present a dorsal segment and a ventral segment as indicated in FIG. 9.

Thereafter, an extension member or segment 24 may be positioned and interposed between the severed segments of the nipple replica 16. In a preferred mode of performance of the inventive method, the provided extension member 24 has a dorsal to ventral length dimension between ¼ inches and ¾ inches. Also in such preferred mode, the diameter of the extension 24 substantially matches the diameters of the nipple replication 18 and the natural nipple 11. Just as the natural and replicated nipples 11 and 18 are substantially cylindrical with a circular cross-section shape, the extension 24 is preferably cylindrical and has a circular cross section. A short length of a wood or plastic dowel material may be suitably utilized in fabricating the extension component member 24.

Figure 10:
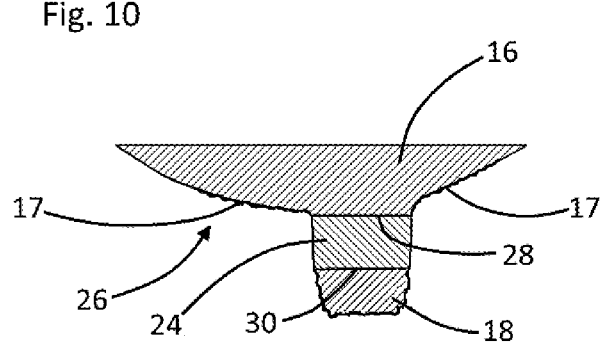
FIG. 10 redepicts the structure of FIG. 9, the view of FIG. 10 showing the exploded view components of FIG. 9 adhesively interconnected.

Thereafter, referring further to FIG. 10, the components depicted in exploded view in FIG. 9 may be reassembled as indicated in FIG. 10. Preferably such components are adhesively bonded at seams 28 and 30 to form a second positive mold 26. Such second positive mold preferably constitutes and serves as a length extended replica of the nursing mother's nipple 10.

Figure 6:
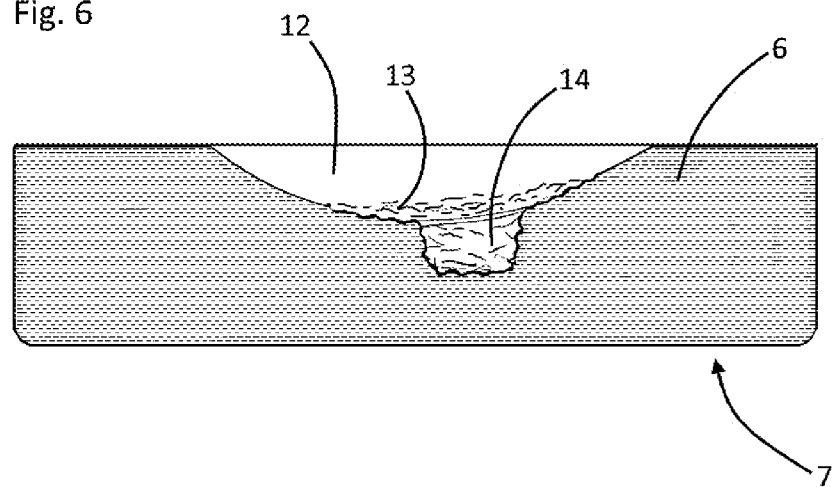
FIG. 6 redepicts the structure of FIG. 5, the view of FIG. 6 showing the solidified mold forming material of FIG. 5 removed from the vessel of FIG. 5.
Figure 11:
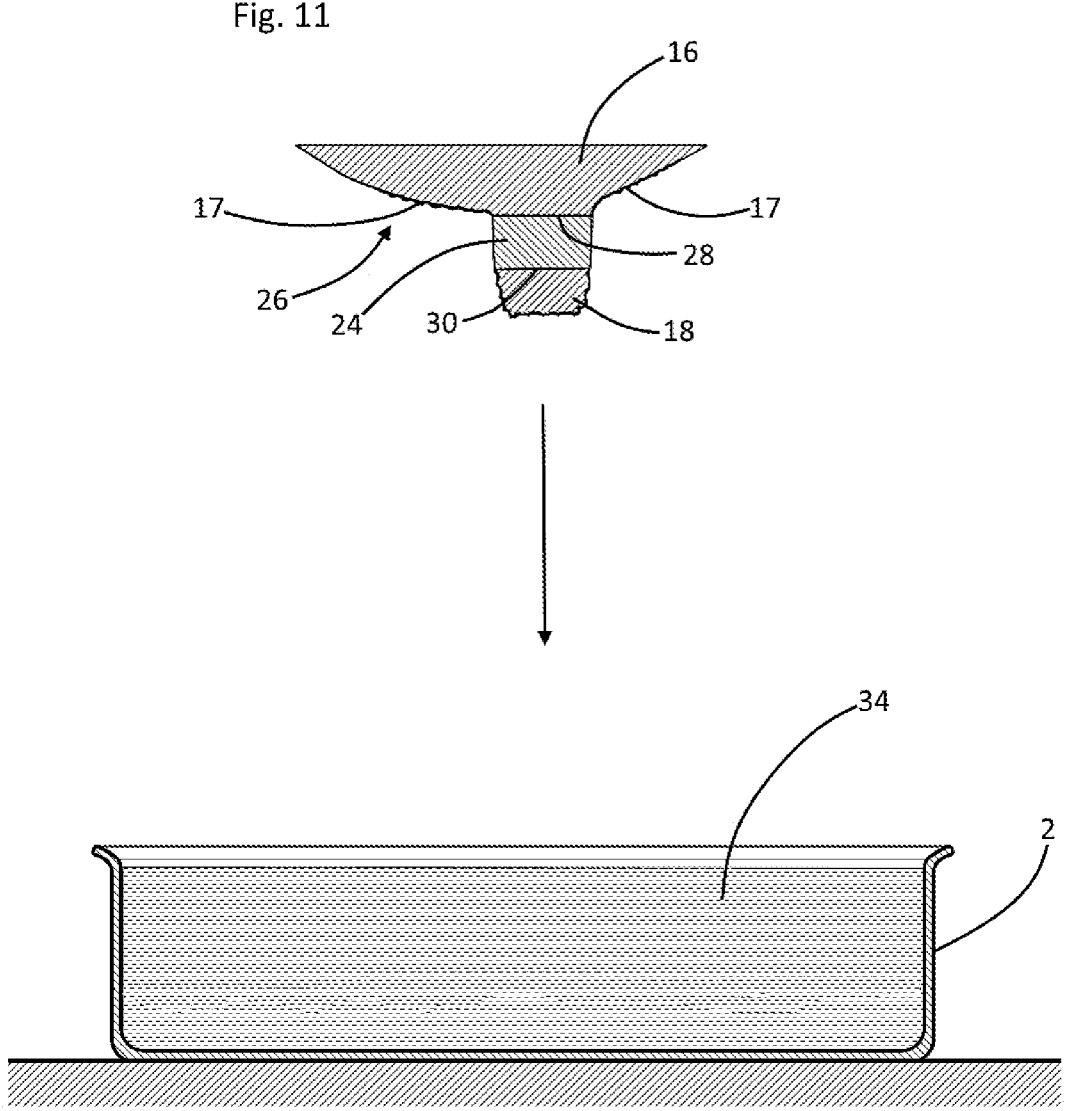
FIG. 11 shows the assembled nipple replication of FIG. 10 overlying the vessel of FIG. 1, such vessel having been refilled with a volume of semi-liquid molding material.
Figure 12:
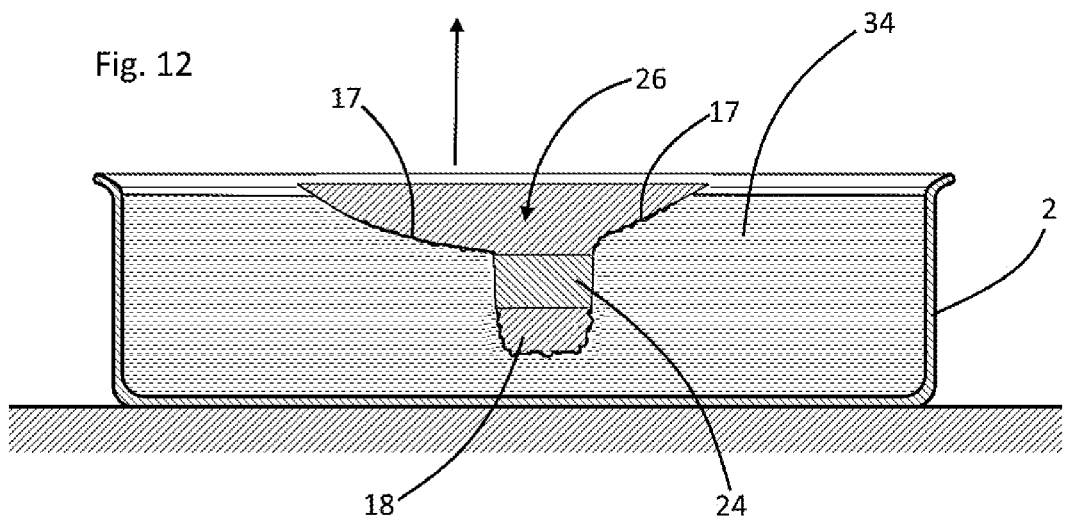
FIG. 12 redepicts the structure of FIG. 11, the view of FIG. 12 showing the assembled nipple replication of FIG. 10 downwardly extended into semi-liquid molding material.
Figure 13:
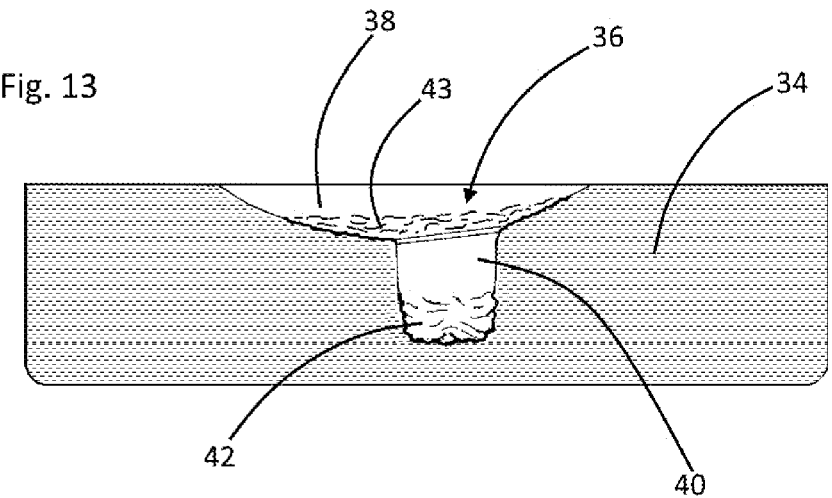
FIG. 13 redepicts the structure of FIG. 12, the view of FIG. 13 showing the assembled nipple replication of FIG. 10 upwardly removed from the molding material.

Thereafter, referring further to FIG. 11 the length extended nipple replica 26 may be positioned, as indicated, above the vessel 2, such vessel having been refilled with a semi-liquid molding material 34. Referring further to FIG. 12 the extended replica 26 may then be downwardly extended and impressed into molding material 34. Upon setting of the molding material 34, the length modified replica 26 may be upwardly removed, leaving a molding void or concavity 36. Such concavity 36 advantageously constitutes a second negative mold which includes a surface textures 42 which substantially exactly replicates the mother's natural nipple texture 10, and includes dorsally overlying surface textures 43 which match and replicate the surface texture 11 of the mother's areola. Referring simultaneously to FIGS. 6 and 13, the first and second negative molds 6 and 36 are preferably substantially identical to each other with the exception that the second negative mold 36 includes a concavity deepening nipple extension section or portion 40.

Figure 14:
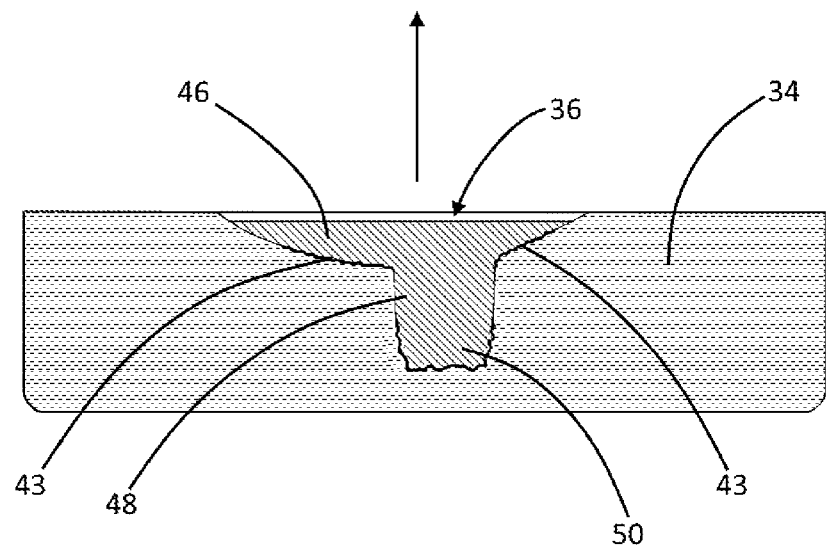
FIG. 14 redepicts the structure of FIG. 13, the view of FIG. 14 showing the molding concavity of FIG. 13 filled with a thermosetting plastic material.
Figure 15:
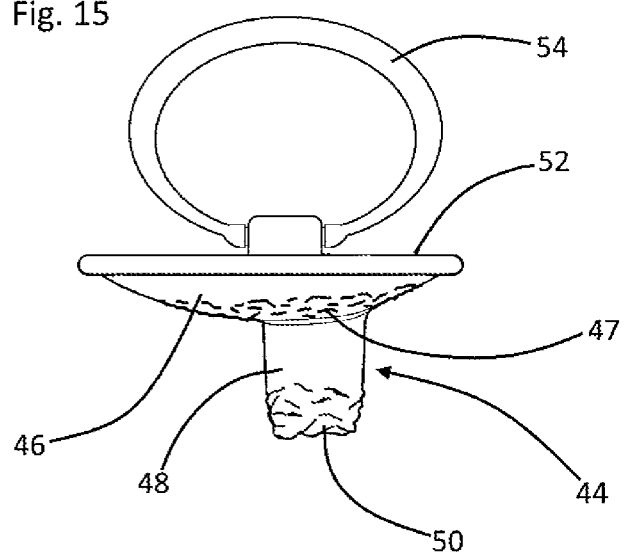
FIG. 15 shows the extended nipple replication FIG. 14 attached to a mouth guard and handle for use as an infant pacifier.

Referring further to FIGS. 14 and 15, the second negative molding concavity 36 may be filled with a thermosetting plastic material 46, suitably silicone, to cast and form an extended replica 46, 50 of the mother's natural nipple 10. The areola portion 46 the finally cast replica advantageously functions as a pacifier mouth guard or shield, while further advantageously presenting indentations and protrusions 43 matching those of the mother's natural areola. Nipple indentations and protrusions 50 of the finely cast nipple portion 44 similarly substantially exactly match the texture of the mother's natural nipple 10. The extension section 48 of the finally cast nipple and areola/mouth shield combination 44 is advantageously formed wholly and seamlessly with other components, reducing the risk of breaking during suckling use by the infant.

In order to better adapt the finally cast nipple and areola/mouth guard combination 44 for use as an infant pacifier, a plastic backing or base 52 may be adhesively attached to the dorsal side of the combination's areola replicating mouth shield section 46. For sanitary handling of the pacifier, a handle 54 may be fixedly attached to such base 52.

Functional benefits of the instant inventive method may be understood by reference to the mechanical effects of an infant's suckling upon the mother's breast 8. Upon the infant's "latch on" oral engagement of her lips with nipple 10, suction imposed at and within the infant's mouth tends to ventrally stretch nipple 10, while simultaneously causing the areola 11 to elastically deflect ventrally into the infant's mouth. Such stretching and deflection naturally increases the effective dorsal to ventral length of the nipple within the infant's mouth while the infants lips and tongue tactilely contact and tactilely perceive the unique surface textures of the mother's areola 11 and nipple 10. The infant pacifier 44, which is produced in accordance with the method steps of the instant invention, includes nipple textures 50 and areola textures 47 that match the corresponding textures 10 and 11 of the mother's breast 8. However, in contrast with the effects of the infant's suckling action upon the natural breast 8, oral vacuum pressure exerted by the infant against the nipple 44 results in only small or negligible amounts of dorsal to ventral stretching of the nipple section 48, and results in a negligible amount of ventral deflection of the areola portion. The instant inventive method accommodates such lack of ventral stretching and deflection by casting as an integral part of the pacifier 44 the extension section or portion 48. The dorsal to ventral length of the extension member 34 and the extension section 48 may advantageously match the effective dorsal to ventral extension of the natural nipple 10 during infant suckling.

Accordingly, the instant inventive method advantageously produces a pacifier which replicates the surface textures of a nursing mother's natural nipple and areola, and further replicates the dorsal to ventral length of such nipple during suckling. Both of the texture and length characteristics of the pacifier are tacitly felt by the infant, and such characteristics are advantageously perceived by the infant as tacitly matching the infant's suckling upon the mother's natural nipple. The dual texture and length aspects of natural nipple replication which are served by the instant inventive method advantageously promote pacifier acceptance by the infant.

While the principles of the invention have been made clear in the above illustrative embodiment, those skilled in the art may make modifications to the method steps, structures, arrangement, portions and provided components of the invention without departing from those principles. Accordingly, it is intended that the description and drawings be interpreted as illustrative and not in the limiting sense, and that the invention be given a scope commensurate with the appended claims.

The invention hereby claimed is:

1. A method for fabricating a pacifier having surfaces matching those of a nursing mother's nipple, said nipple having a length, said method comprising steps of:
   (a) utilizing the nursing mother's nipple as a positive mold to cast a first negative mold;
   (b) utilizing the first negative mold to cast replica of the nursing mother's nipple;
   (c) modifying the replica of the nursing mother's nipple so that said replica has a length greater than that of the nursing mother's nipple;
   (d) utilizing the modified replica of the nursing mother's nipple as a second positive mold to cast a second negative mold; and
   (e) utilizing the second negative mold to cast an extended replica of the nursing mother's nipple.

2. The method of claim 1 wherein the utilizing the nursing mother's nipple as a positive mold to cast a first negative mold step comprises an insertion of the nursing mother's nipple into a semi-liquid molding material.

3. The method of claim 2 wherein the modifying the replica of the nursing mother's nipple so that said replica has a length greater than that of the nursing mother's nipple step comprises steps of providing an extension, segmenting the replica of the nursing mother's nipple, positioning the extension between said replica's segments, and fixedly attaching said replica's segments at opposite ends of the extension.

4. The method of claim 3 further comprising a step of fixedly attaching a pacifier mouth shield to a dorsal end of the extended replica of the nursing mother's nipple.

5. The method of claim 4 further comprising a step of attaching a handle to a dorsal side of the pacifier mouth shield.

6. The method of claim 3 wherein the nursing mother's nipple has a diameter, and wherein the extension providing step comprises a provision of a cylindrical member having a diameter substantially equal to the diameter of the nursing mother's nipple.

7. The method of claim 6 wherein the cylindrical member has a length between ¼ and three ¾ inches.

8. The method of claim 2 wherein the step of inserting the nursing mother's nipple into the semi-liquid molding material is followed by a step of inserting the nursing mother's areola into said material, the first negative mold being thereby adapted to form, as a part of the replica of the nursing mother's nipple, a replica of said areola.

9. The method of claim 8 further comprising a step of forming a mouth shield at a dorsal end of the extended replica of the nursing mother's nipple, said mouth shield comprising the replica of the nursing mother's areola.

10. The method of claim 2 wherein the semi-liquid molding material is selected from the group of materials consisting of alginate, silicon, polyurethane resin, latex, urethane resin, plaster, and epoxy resin.

11. The method of claim 10 wherein an upwardly opening vessel is provided, and wherein the selected semi-liquid molding medium is contained within said vessel.

12. The method of claim 11 wherein the step of inserting the nursing mother's nipple into the semi-liquid molding material comprises downwardly moving said nipple into the upwardly opening vessel.

* * * * *